United States Patent [19]

Beaver

[11] Patent Number: 5,025,110

[45] Date of Patent: Jun. 18, 1991

[54] ALCOHOL REACTION MEDIA FOR PRODUCTION OF HEXABROMOCYCLODODECANE

[75] Inventor: Phillip R. Beaver, Baton Rouge, La.

[73] Assignee: Ethyl Corporation, Richmond, Va.

[21] Appl. No.: 475,445

[22] Filed: Feb. 6, 1990

[51] Int. Cl.$^5$ .............................................. C07C 17/10
[52] U.S. Cl. .................................... 570/206; 570/208
[58] Field of Search ................ 570/206, 207, 208, 213

[56] References Cited

U.S. PATENT DOCUMENTS

| | | | |
|---|---|---|---|
| 3,558,727 | 1/1971 | Jenkner et al. | 260/648 |
| 3,652,688 | 3/1972 | Olechowski et al. | 260/648 |
| 3,833,675 | 9/1974 | Newcombe et al. | 260/648 |
| 4,783,563 | 11/1988 | Taniuchi et al. | 570/246 |

FOREIGN PATENT DOCUMENTS

| | | | |
|---|---|---|---|
| 0181414 | 11/1984 | European Pat. Off. | 570/206 |
| 3120621 | 5/1981 | Fed. Rep. of Germany | 570/206 |
| 50-5187 | 2/1975 | Japan | 570/206 |
| 2205830 | 12/1988 | United Kingdom | 570/206 |

*Primary Examiner*—Werren B. Lone
*Attorney, Agent, or Firm*—Terry B. Morris

[57] ABSTRACT

Composition of solvents usable for the production of hexabromocyclododecane and methods of use of such compositions are disclosed. The compositions comprise $C_5$–$C_8$ saturated aliphatic alcohols having low mutual solubility with water.

19 Claims, No Drawings

ALCOHOL REACTION MEDIA FOR PRODUCTION OF HEXABROMOCYCLODODECANE

FIELD OF THE INVENTION

This invention relates to compositions and methods for the manufacture of hexabromocyclododecane.

BACKGROUND

Methods of bromination of cyclododecatriene (e.g. trans,trans,trans- or trans,trans,cis-1,5,9-cyclododecatriene or mixtures thereof) in solvent(s) to produce hexabromocyclododecane ("HBCD" hereinafter) are known. For examples of prior art teaching bromination of cyclododecatriene to product HBCD in solvent media of lower alcohols (i.e. $C_1$–$C_4$) and/or halogenated hydrocarbons, see U.S. Pat. Nos. 3,558,727 (Jenkner et al) and 3,833,675 (Newcombe et al). After the bromination reaction, the reaction mass can be subjected to separation techniques (e.g. filtration centrifugation or decantation) to produce a recovered mass, which is predominantly HBCD particles but which can additionally contain contaminants to this product, and to recover solvent for reuse. For examples of such techniques, see (Jenkner et al) U.S. Pat. No. 3,558,727 and U.K. 2,205,830 (Hermolin et al). The use of a relatively higher alcohol (i.e. $C_4$–$C_8$) solvent media is taught in (Taniuchi et al) U.S. Pat. No. 4,783,563, but only in conjunction with a catalytic complex (i.e. boron trifluoride complex). There continues to be a need for new solvent medias and processes for the bromination of cyclododecatriene to produce HBCD as well as techniques to recover and/or recycle solvent components for reuse.

SUMMARY

Improved methods have been discovered for brominating cyclododecatriene to produce HBCD as well as recovering solvent for reuse. The methods comprise the use of a higher alcohol (preferably $C_5$–$C_8$ saturated linear or branched aliphatic alcohols having low solubility in water) in the bromination solvent composition. These methods can provide an HBCD product without the requirement of a catalyst and also can permit the recovery of solvent for reuse.

DESCRIPTION OF THE PREFERRED EMBODIMENTS

The embodiments of the present invention comprise solvent compositions for the bromination of cyclododecatriene to produce hexabromocyclododecane and methods for use of such solvent compositions in such bromination. These compositions and methods of producing HBCD comprise the use of an alcohol having limited solubility with water. Both limits of solubilities (i.e. the solubility of the alcohol in water and the solubility of the water in alcohol) can be present (i.e. limited mutual solubility) and are preferably both present. In the preferred embodiments, the solvent composition comprises one or more $C_5$–$C_8$ saturated aliphatic alcohols, whereineach of said one or more alcohols has a solubility in water at 25° C. of about 5 weight percent or less or water has a solubility in each of said one or more alcohols at 25° C. of about 15 weight percent or less. Mixtures of the embodied alcohols can be used, which include mixtures of two or more of linear or branched $C_5$–$C_8$ saturated aliphatic alcohols or mixtures of other alcohols and one or more linear or branched $C_5$–$C_8$ saturated aliphatic alcohols.

Unexpectedly, the improved methods of the current invention allows use of a higher alcohol without the necessity of a catalyst to provide a high yield of a hexabromocyclododecane product having a high melting point. The improved methods have advantages in solvent recovery through the limited solubilities of water and solvent components.

Preferred saturated aliphatic alcohols in accordance with embodiments of the invention include 1-pentanol-(amy alcohol), 3-methyl-1-butanol(isoamyl alcohol), cyclohexanol, 1-hexanol(n-hexyl alcohol), 4-methyl-2-amyl alcohol, 2-ethyl butyl alcohol(sec-hexyl alcohol), benzyl alcohol, and 2-ethyl hexanol. The more preferred alcohol is 2-ethyl hexanol. These alcohols have an additional advantage in their azeotropic characteristics with water in recovery or purification processes, such as those methods shown, for example, in U.S. application Ser. No. 457,960 filed Dec. 27, 1989 by P. Beaver, P. DiGiacinto, D. Hutchinson and J. Vega, filed concurrently herewith, the disclosure which is hereby incorporated by reference.

Compositions in accordance with the embodiments of the present invention can replace the solvent compositions typically used in the bromination of cyclododecatriene to produce hexabromocyclododecane. Illustrative of such prior art bromination of cyclododecatriene are U.K. 2,205,830 (Hermolin et al) and (Jenkner et al) U.S. Pat. No. 3,558,727, incorporated in their entirety herein by reference. Embodiments of the solvent composition can additionally comprise the admixture of a halogenated hydrocarbon with the embodied alcohol. Illustrative of such prior art halogenated hydrocarbons are those found in (Jenkner et al) U.S. Pat. No. 3,558,727 and Japanese Patent Publication No. (Kokuku) 50-5187 (Kawaguchi et al), both references incorporated herein by reference. Non-limiting examples of such halogenated hydrocarbons include carbon tetrachloride, chloroform, isobutyl bromide, ethylene dichloride and dibromomethane.

Embodiments of the invention further include methods for the bromination of cyclododecatriene to produce hexabromocyclododecane comprising the step of brominating cyclododecatriene in a solvent mixture comprising an alcohol and a halogenated hydrocarbon, said alcohol and halogenated hydrocarbon preferably being in a ratio of about 99 alcohol/1 halogenated hydrocarbon by weight to about 30 alcohol/70 halogenated hydrocarbon by weight, more preferably about 75 weight units alcohol to about 25 weight unit halogenated hydrocarbon, and the alcohol being a $C_5$–$C_8$ saturated aliphatic alcohols wherein at 25° C. the alcohol has a solubility in water of about 5 weight percent or less or wherein at 25° C. water has a solubility in the alcohol of about 15 weight percent or less, more preferably wherein at 25° C. the alcohol has a solubility in water of about 5 weight percent or less and water has a solubility in the alcohol of about 15 weight percent or less. Embodiments of the invention which include methods for the bromination of cyclododecatriene to produce hexabromocyclododecane comprise brominating cyclododecatriene in a reaction mixture comprising about 30 to about 50 weight percent alcohol, about 5 to about 20 weight percent halogenated hydrocarbon, about 30 to about 50 weight percent bromine and about 5 to about 20 weight percent cyclododecatriene. Preferably the ratio of alcohol to halogenated hydrocarbon ranges from about 99/1 to about 30/70, more preferably about 90/10 to about 50/50, most preferably about 75/25.

Preferred halogenated hydrocarbons are carbon tetrachloride, chloroform, dibromomethane, trichloroethylene, ethylene dichloride, 2-ethyl hexylbromide and ethylene bromide. A more preferred halogenated hydrocarbon is ethylene dichloride. Preferred solvents are mixtures of 2-ethyl hexanol and ethylene dichloride and mixtures or 2-ethyl hexanol and 2-ethyl hexyl bromide, each preferably in respective weight ratios of about 75 to 25.

The ratio of bromine to cyclodedecatriene should be in a stoichiometric amount of about 3 mols/1 mol more preferably with a slight excess of bromine, e.g. about 0 to about 8 weight percent bromine in excess. In a process where bromine and cyclododecatriene are admixed in a solvent-containing reaction vessel in accordance with the present invention, preferably the addition of bromine is kept slightly ahead stoichiometrically of the addition of cyclododecatriene, as by a slight pre-charging of bromine into the solvent mixture. Additionally, the solvent mixture need not be added all at once initially into the reaction vessel. About 5 to about 30% of the solvent mixture (e.g. the alcohol and halogenated hydrocarbon) may be added before the feed of the reactants into the reaction vessel. The balance of the solvent may then be added with the reactants.

The present invention can use the various addition and mixing schemes of the reactants and solvent mixtures which are known already in the art. The solvent mixture in accordance with the embodiments in the present invention can be precharged into the reactor vessel before introduction of one or more of the reactants. Separate or combined feed streams of the solvent and one or both reactants can also be used. Preferably, a slight excess of bromine can be precharged to the reaction vessel. For examples of feed stream strategies relevant to hexabromocyclododecane production see (Jenkner et al) U.S. Pat No. 3,558,727. Reaction times, temperatures, pressures and loading can be the same as those already used in the art; however, the present invention can work satisfactorily at the higher temperatures, e.g. about 60° C., as opposed to prior art schemes which-preferred lower temperatures, e.g. 10° C. to 40° C., for satisfactory performances.

Advantages found in yet further embodiments of the present invention include methods to recover or recycle the alcohol used by use of separation techniques which take advantage of the limited mutual solubility of water and the alcohol. After the formation of a reaction mass in accordance with the embodiments of the invention described hereinabove, solvent recovery can be performed. Solvent recovery processes can include nutralization of hydrogen bromide with an aqueous base. This nutralization contaminants the solvents with water. Other process steps, such as steam stripping to recover the product or such as water washing of filter cakes can also introduce water into the system. Because of the low mutual solubility that the embodied alcohols have with the water, liquid-liquid phase separation techniques can be used to recover and recycle the alcohol without the necessity of additional heat. These techniques can include decantation, multiple phase cyclone separators or other such techniques which utilize the liquid-liquid phase separation because of the low mutual solubility of the water and alcohol.

Embodiments of the invention can include the use of heat after an initial phase separation for the recovery of the alcohol even purer form than liquid-liquid phase separation alone. For example, the recovery of 2-ethyl hexanol, when used as a solvent, can be made using azeotropic characteristics of a mixture of water and 2-ethyl hexanol. The water can be present in mixture with a solvent as a by-product or a rinse agent, or even added for recovery purposes. An azeotrope of water and 2-ethyl hexanol has a boiling point of 99.1° C., which is below the boiling point range of 184° C. for 2-ethyl hexanol alone. This azeotrope produces on distillation an azeotropic condensate having an upper level phase consisting of 97.4% 2-ethyl hexanol and 2.6% water, and a lower phase 0.1% 2-ethyl hexanol and 99.9% water. These phases can then be subjected to a liquid-liquid phase separation (e.g. decantation) to permit the recovery of relatively pure alcohol and pure water. The alcohol is recyclable for use in the process.

The following examples illustrate the embodiments of the invention in comparison with prior art methods. The examples are not intended to limit the invention to a particular set of parameters.

EXAMPLE 1

A pot was charged with 29.9 grams of 2-ethyl hexanol and 10.1 grams of ethylene dichloride. From a feed flask, 159.9 grams of bromine ($Br_2$) 50.0 grams of cyclododecatriene, 112.5 grams of 2-ethyl hexanol and 37.6 grams of ethylene dichloride were fed into the pot over the next 60 minutes at 60° C. forming a reaction mass. Neutralization with 11.0 grams of monoethanolamine was then performed to a pH of 7. The mass was then quick cooled to 19° C. and filtered, removing 153.1 grams of the mother liquor. Washing with 208.8 grams of water produced a wet cake of 232.5 grams, subsequently dried to 158.0 grams of product. The product yield was 80% with a melting point of 185° C.

EXAMPLE 1 (Comparative)

A pot was charged with 5.0 grams of ethanol and 15.2 grams of ethylene dichloride. While keeping bromine in slight excess, 154.9 grams of bromine ($Br_2$) and from a feed flask 51.1 grams of cyclododecatriene (CDT), 25.6 grams of ethanol and 76.0 grams of ethylene dichloride were fed into the pot over the next 50 minutes at 45° C. forming a reaction mass. Nine grams of ethanol were used to flush the feed flask. The mass was cooked for 30 minutes at 45° C. Neutralization with 6.6 grams of monoethanolamine was then performed to a pH of 7.5. The mass was then quick cooled to 19° C. and filtered, removing 96 grams of the mother liquor. Washing with 213.8 grams of water produced a wet cake of 193.5 grams, subsequently dried to 142.6 grams of product. The product yield was 70% with a melting point of 186°–189° C.

EXAMPLE 2 (Comparative)

A pot was charged with 5.3 grams of ethanol and 15.8 grams of ethylene dichloride. While keeping bromine in slight excess, 150.1 grams of bromine ($Br_2$) and from a feed flask 50.0 grams of cyclododecatriene (CDT), 42.5 grams of ethanol and 130.9 grams of ethylene dichloride were fed into the pot over the next 55 minutes at 45° C. forming a reaction mass. Ten and 1/10 grams of ethanol were used to flush the feed flask. The mass was cooked for 30 minutes at 45° C. Neutralization with 7.1 grams of monoethanolamine was then performed to a pH of 7.0. The mass was then quick cooled to 19° C. and filtered, removing 210.4 grams of the mother liquor. Washing with 203.1 grams of water produced a wet cake of 160.2 grams, subsequently dried to 122.7 grams of product. The product yield was 62% with a melting point of 189°–191° C.

EXAMPLE 3 (Comparative)

A pot was charged with 20.0 grams of isobutanol and 20.5 grams of ethylene dichloride. While keeping bromine in slight excess, 150.2 grams of bromine ($Br_2$) and from a feed flask 50.0 grams of cyclododecatriene (CDT), 69.9 grams of isobutanol and 70.6 grams of ethylene dichloride were fed into the pot over the next 60 minutes at 45° C. forming a reaction mass. Ten and 2/10 grams of isobutanol were used to flush the feed flask. The mass was cooked for 30 minutes at 45° C. Neutralization with 5.8 grams of monoethanolamine was then performed to a pH of 7.0. The mass was then quick cooled to 19° C. and filtered, removing 156.0 grams of the mother liquor. Washing with 218.7 grams of water produced a wet cake of 205.4 grams, subsequently dried to 141.0 grams of product. The product yield was 71% with a melting point of 186°–190° C.

EXAMPLE 4 (Comparative)

A pot was charged with 10.0 grams of isobutanol and 31.5 grams of ethylene dichloride. While keeping bromine in slight excess, 153.0 grams of bromine ($Br_2$) and from a feed flask 50.2 grams of cyclododecatriene (CDT), 38.5 grams of isobutanol and 112.2 grams of ethylene dichloride were fed into the pot over the next 40 minutes at 60° C. forming a reaction mass. Fourteen and ½ grams of isobutanol were used to flush the feed flask. The mass was cooked for 45 minutes at 60.C. Neutralization at 60° C. with 8.4 grams of monoethanolamine was then performed to a pH of 7.0. The mass was then quick cooled to 19° C. and filtered, removing 219.0 grams of the mother liquor. Washing with 202.2 grams of water produced a wet cake of 156.6 grams, subsequently dried to 122.6 grams of product. The product yield was 62% with a melting point of 189°–193° C.

EXAMPLE 5 (Comparative)

A pot was charged with 20.0 grams of isobutanol and 20.3 grams of ethylene dichloride. While keeping bromine in slight excess, 163.1 grams of bromine ($Br_2$) and from a feed flask 50.1 grams of cyclododecatriene (CDT), 70.1 grams of isobutanol and 70.3 grams of ethylene dichloride were fed into the pot over the next 50 minutes at 60° C. forming a reaction mass. The mass was cooked for 50 minutes at 60° C. Neutralization was not performed. The mass was then filtered, removing 209.6 grams of the mother liquor. Washing with 1068.9 grams of water produced a wet cake of 178.1 grams, subsequently dried to 137.8 grams of product. The product yield was 69% with a melting point of 189°–191° C.

EXAMPLE 6 (Comparative)

A pot was charged with 19.9 grams of isobutanol and 20.1 grams of ethylene dichloride. From a feed flask, 155.2 grams of bromine ($Br_2$), 49.9 grams of cyclododecatriene (CDT), 70.1 grams of isobutanol and 69.8 grams of ethylene dichloride were fed into the pot over the next 48 minutes at 45° C. forming a reaction mass. Nine grams of isobutanol were used to flush the feed flask. The mass was cooked for 45 minutes at 45°C. The mass was heated to 60° C. and 3.6 grams of water were added. Neutralization with 5 grams of sodium carbonate was then performed. The mass was then quick cooled to 19° C. and filtered, removing 135.2 grams of the mother liquor. Washing with 418.6 grams of water produced a wet cake of 217.7 grams, subsequently dried to 139.8 grams of product. The dried product yield was 71% with a melting point of 186°–190° C.

What is claimed is:

1. A solvent composition comprising
   (a) one or more $C_5$–$C_8$ saturated linear or branched aliphatic alcohols, wherein each of said one or more alcohols independently has a solubility in water at 25° C. of about five weight percent or less or water has a solubility in each of said one or more alcohols at 25° C. of about fifteen weight percent or less, or
   (b) one or more $C_5$–$C_8$ saturated linear or branched aliphatic alcohols, wherein each of said one or more alcohols independently has a solubility in water at 25° C. of about five weight percent or less or water has a solubility in each of said one or more alcohols at 25° C. of about fifteen weight percent or less and one or more halogenated hydrocarbons.

2. The composition of claim 1 wherein said one or more alcohols is selected from a group consisting of 1-pentanol, 3-methyl-1-butanol, cyclohexanol, 1-hexanol, 4-methyl-2-amyl alcohol, 2-ethyl butyl alcohol, benzyl alcohol and 2-ethyl hexanol.

3. The composition of claim 2 wherein said alcohol is 2-ethyl hexanol.

4. The composition of claim 1 wherein said halogenated hydrocarbon is selected from a group consisting of carbon tetrachloride, chloroform, dibromomethane, trichloroethylene, ethylene bromide, ethylene dichloride and 2-ethyl hexyl bromide.

5. The composition of claim 4 wherein said halogenated hydrocarbon is ethylene dichloride.

6. The composition of claim 4 wherein said halogenated hydrocarbon is 2-ethyl hexyl bromide.

7. The composition of claim 1 wherein the weight ratio of said one or more alcohols to one or more halogenated hydrocarbon is from about 99/1 to about 30/70.

8. The composition of claim 7 wherein said ratio is about 75/25.

9. The composition of claim 1 wherein each of said one or more alcohols independently has a solubility in water at 25° C. of about five weight percent or less and water has a solubility in each of said one or more alcohols at 25° C. of about fifteen weight percent or less.

10. A method for the bromination of cyclododecatriene to produce hexabromocyclododecane comprising the step of
    brominating cyclododecatriene with bromine in a solvent mixture comprising one or more alcohols and one or more halogenated hydrocarbons, said one or more alcohols and one or more halogenated hydrocarbons being in a weight ratio of said alcohol(s) to said halogenated hydrocarbon(s) of from about 99/1 to about 30/70,
    and each of said one or more alcohols being a $C_5$–$C_8$ saturated linear or branched aliphatic alcohol wherein at 25° C. each of said alcohol independently has a solubility in water of about 5 weight percent or less and/or wherein at 25° C. water has a solubility in said alcohol of about 15 weight percent or less.

11. The method of claim 10 wherein said one or more alcohols is selected from a group consisting of 1-pentanol, 3-methyl-1-butanol, cyclohexanol, 1-hexanol, 4-methyl-2-amyl alcohol, 2-ethyl butyl alcohol, benzyl alcohol and 2-ethyl hexanol.

12. The method of claim 11 wherein said alcohol is 2-ethyl hexanol.

13. The method of claim 11 wherein said solvent composition further comprises one or more halogenated hydrocarbon.

14. The method of claim 13 wherein said halogenated hydrocarbon is selected from a group consisting of carbon tetrachloride, chloroform, dibromomethane, trichloroethylene, ethylene bromide and ethylene dichloride.

15. The method of claim 14 wherein said halogenated hydrocarbon is ethylene dichloride.

16. The method of claim 14 wherein said halogenated hydrocarbon is 2-ethyl hexyl bromide.

17. The method of claim 14 wherein the weight ratio of said one or more alcohols to one or more halogenated hydrocarbon is from about 99/1 to about 30/70.

18. The method of claim 17 wherein said ratio is about 75/25.

19. The method of claim 10 wherein the bromination of cyclododecatriene is at a temperature above about 10° C.

* * * * *